United States Patent
Miroshnychenko et al.

(10) Patent No.: US 7,341,708 B1
(45) Date of Patent: *Mar. 11, 2008

(54) METHODS FOR PRODUCING PURE AMINO ACID CHELATE COMPLEXES, AND USES THEREOF

(76) Inventors: Oleksandr Miroshnychenko, 13880 Viking Place, Richmond, British Columbia (CA) V6V 1K8; Xueju Xie, 13880 Viking Way, Richmond, British Columbia (CA) V6V 1K8; Jason Jiang-Chung Ko, 13880 Viking Place, Richmond, British Columbia (CA) V6V 1K8

( * ) Notice: Subject to any disclaimer, the term of this patent is extended or adjusted under 35 U.S.C. 154(b) by 0 days.

This patent is subject to a terminal disclaimer.

(21) Appl. No.: 11/613,963

(22) Filed: Dec. 20, 2006

Related U.S. Application Data

(63) Continuation-in-part of application No. 11/583,817, filed on Oct. 20, 2006.

(51) Int. Cl.
*A61K 51/00* (2006.01)
*A61M 36/14* (2006.01)

(52) U.S. Cl. .................... 424/1.65; 424/1.11; 424/1.65

(58) Field of Classification Search ............... 424/1.11, 424/1.65, 1.69; 534/7, 10–16; 530/300, 530/324–331, 333, 338, 344, 317
See application file for complete search history.

(56) References Cited

U.S. PATENT DOCUMENTS

| | | | |
|---|---|---|---|
| 6,114,379 | A | 9/2000 | Wheelwright et al. |
| 6,458,981 | B1 | 10/2002 | Ashmead et al. |
| 7,087,775 | B2 | 8/2006 | Lee et al. |
| 7,129,375 | B2 | 10/2006 | Abdel-Monem et al. |
| 7,141,689 | B2 | 11/2006 | Abdel-Monem et al. |
| 2004/0097748 | A1 | 5/2004 | Abdel-Monem et al. |

*Primary Examiner*—Dameron L. Jones
(74) *Attorney, Agent, or Firm*—Fasken Martineau

(57) ABSTRACT

A two-stage method of preparing essentially pure amino acid chelates, wherein the first stage comprises contacting a metal ion from a metal oxide or hydroxide with an amino acid thereby producing a metal hydroxyl amino acetate. The second stage comprises contacting the metal hydroxyl amino acetate from the first stage, with at least one amino-containing compound provided in excess thereby producing a reaction solution containing an amino acid chelate reaction product comprising a metal ion bound to a plurality of amino acid ligands wherein the plurality of amino acid ligands is equal to the coordination number of the metal ion, and then separating the amino acid chelate from the reaction solution. The second stage may include a plurality of steps for sequentially reacting the reaction product with a plurality of amino-containing compounds. The amino acid chelates thus produced can be incorporated into compositions comprising beverages, foodstuffs, nutraceuticals and pharmaceutical adjuvants.

2 Claims, No Drawings

METHODS FOR PRODUCING PURE AMINO ACID CHELATE COMPLEXES, AND USES THEREOF

CROSS-REFERENCE TO RELATED APPLICATIONS

This Continuation-in-Part Application claims priority from our Utility application Ser. No. 11/583,817 filed Oct. 20, 2006, currently pending.

FIELD OF THE INVENTION

This invention relates to methods of preparing amino acid chelates and complexes, and uses thereof. More particularly, this invention relates to methods of preparing essentially pure amino acid chelates that are highly soluble over a wide pH range and are stable in solutions for extended periods of time.

BACKGROUND OF THE INVENTION

The supply of proper levels of bioavailable essential minerals in daily diets is important for maintaining human health. It is well known that, for example, calcium deficiencies may induce osteoporosis, immunological diseases, hypertension, arthritis, colon cancer, diabetes, and obesity, while zinc deficiencies may result in prolonged healing of wounds, retarded growth, delayed sexual maturity, post-pregnancy stretch marks, fatigue, and susceptibility to infection.

It is also well known that metals chelated by amino acids are important sources of trace minerals essential for human, animal, and plant nutrition. The health advantages of supplementing nutritional inputs with amino acid chelates for human and animal consumption are well documented in the prior art. Active transport mechanisms for uptake of amino acids by mucosal cells also sequester metals chelated to amino acids an active transport as solely amino acids, whereas such metals supplied in an inorganic form or as organic salts are not readily digestable.

Amino acid chelates refer to the products formed by the reaction of naturally occurring amino acids with metal ions to produce one or more five-member rings with structures that are defined by the metal atom, the carboxyl oxygen, the carbonyl carbon, the α-carbon and the α-amino acid nitrogen moities. However, the actual structure architecture of each amino acid chelate is determined by the coordination number of the central metal ion and the molar ratio of ligand (i.e., amino acid) to metal. The coordination number of a specified atom in a chemical species is the number of other atoms that can be directly linked to that atom in a particular reaction. For example, it is known that the zinc, magnesium and cobalt each have a coordination number of 6, while calcium may have a coordination number of 6 or 8. However, Pidcock and Moore (2001, J. Biol. Inorg. Chem. 6, 479-489) have reported that the average coordination number for $Ca^{2+}$ was 6, based on surveys of X-ray structures of numerous $Ca^{2+}$-containing proteins.

Amino acid chelates are generally produced by first dissolving a water-soluble metal salt in water, and then adding in the amino acid ligand to provide a metal to ligand molar ratio of about 1:1 to 1:4. The water-soluble metal salts used as starting materials for methods to chelate amino acids typically provide the metal complexed to an anion, most commonly sulfate ions or chloride ions. Although some prior art methods provide steps for removal of excess anions during the production of amino acid chelates, significant amounts of anions typically remain trapped within the chelate ring-structures and/or directly bound to the metal cations sequestered within the amino acid rings. Numerous disadvantages are associated with amino acid chelates produced from metal salts wherein anions are bound to the metal cations. For example, ingestion of chelated amino acids for extended periods of time may result in the accumulation of sulfate and/or chloride anions in body tissues to the extent where these anions can negatively affect general health and well being. Amino acid chelates containing significant amounts of anions often exhibit poor solubility and stability properties, particularly in strong acid or alkaline environments, or in the presence of other ions such as phosphates. Furthermore, the presence of anions, such as sulfate or chloride ions, in amino acid chelates can often result in undesirable or objectionable tastes and odors when such amino acid chelates are incorporated into foodstuffs and beverages.

Various approaches have been disclosed in the prior art for ameliorating the disadvantages of amino acid chelates containing anions as a consequence of the methods by which they were produced. For example, U.S. Pat. Nos. 5,504,055 and 6,299,914 teach that the solubility and stability of such amino acid chelates can be improved by adding in pH adjustors and suspension stabilizers during the chelation process. U.S. Pat. No. 6,458,981 discloses a method for reducing the anionic content of amino acid chelate products by supplying along with the desired metal in the form of a metal sulfate salt, a hydroxide or calcium hydroxide for reacting with and precipitating free sulfate ions from the reaction mixture after which, the precipitated calcium sulfate is separated from the amino acid chelate product.

SUMMARY OF THE INVENTION

The exemplary embodiments of the present invention, at least in preferred forms, are directed to methods for producing essentially pure amino acid chelates, amino acid chelates produced by said methods, and compositions containing therein said amino acid chelates.

According a preferred embodiment of the present invention, there is provided a two-stage method for producing an essentially pure amino acid chelate.

According to one aspect, the first stage of the method comprises contacting a metal ion with an amino acid to produce metal hydroxyl amino acetate. It is preferred that the metal ion is provided as a metal oxide or a metal hydroxide.

According to another aspect, the second stage comprises contacting the metal hydroxyl amino acetate produced in the first stage of the method, with at least one amino-containing compound provided in excess thereby producing an amino acid chelate reaction product comprising a metal bound to a plurality of amino acid ligands wherein the number of amino acid ligands bound to the metal ion is equal to the coordination number of the metal. In one preferred form, the amino-containing compound is an amino acid. In another preferred form, the amino-containing compound may be a dipeptide, a tripeptide or a poly peptide.

According to yet another aspect, the second stage may comprise a plurality of steps for sequentially and separately contacting the metal hydroxyl amino acetate produced in the first stage of the method, with a plurality of amino-containing compounds thereby producing an amino acid chelate reaction product comprising a metal bound to a plurality of different amino acid ligands wherein the total number of amino acid ligands bound to the metal ion is equal to the coordination number of the metal. It is preferred that the amino acid ligands include one of aspartic acid or glutamic acid, and that at least two different amino acids ligand are provided. In one preferred form, the amino-containing compounds may be amino acids. In another preferred form, the amino-containing compounds may be dipeptides, tripeptides or apoly peptides. In yet another preferred form, the amino-containing compounds may be a combination of amino acids, dipeptides, tripeptides and polypeptides.

According to a further aspect, the amino acid chelate reaction product is separated from the reaction solution and dried.

According to another preferred embodiment of the present invention, there are provided essentially pure amino acid chelates produced by the methods of the present invention. According to one aspect, the amino acid chelates are essentially free from any extraneous ions as exemplified by sulfate and chloride ions, and therefore are essentially taste-free. The amino acid chelates of the present invention are highly soluble over a broad pH range, and are stable in solution for extended periods of time. The amino acid chelates of the present invention can be easily solubilized without the need for addition of supplemental solubilizing agents and/or pH adjusters.

According to yet another preferred embodiment of the present invention, there are provided compositions containing therein the amino acid chelates of the present invention produced by the methods of the present invention. Such compositions may include beverages, foodstuffs, nutritional supplements, nutraceuticals and pharmaceutical adjuvants.

According to one aspect, the beverages may comprise extracts or juices or other preparations from plant materials such as fruits, seeds, tubers, stems and leaves among others.

According to another aspect, the beverages may comprise dairy products or alternatively, dairy-substitute products.

DETAILED DESCRIPTION OF THE INVENTION

The present invention provides methods for the production of pure amino acid chelates, pure amino acid chelates produced by said methods, and compositions containing therein said pure amino acid chelates. The pure amino acid chelates produced by the methods of the present invention are highly soluble in a wide variety of solvents having pHs from the range of 2 to 11. Furthermore, solubilized pure amino acid chelates of the present invention are stable, i.e., do not precipitate out of solution, for extended periods of time over a broad range of storage temperatures, or when exposed to highly reactive anions such as phosphate.

As used herein:

"Amino acid chelate" refers to a metal ion bonded to amino acid ligands thereby forming a heterocyclic ring.

"Pure amino acid chelate" means that there are no extraneous cations or anions as exemplified by hydroxyl, sulphate and chloride ions, associated with and/or bound to and/or sequestered within the amino acid chelates produced by the methods of the present invention. Furthermore, "pure amino acid" means that the coordination number of the central metal ion in the heterocyclic ring is completely bound by electron donor groups provided only from amino acid ligands which formed ionic and/or a valence and/or coordinate covalent bonds with the central metal ion.

"Coordination number" of a specified metal atom means the total number of other atoms that can be directly linked to that metal atom during a chelation reaction.

"Amino acid ligand" means any of the naturally occurring amino acids including alanine, arginine, asparagine, aspartic acid, cysteine, cystine, glutamic acid, glutamine, glycine, histidine, isoleucine, leucine, lysine, methionine, ornithine, phenylalanine, proline, serine, threonine, tryptophane, tyrosine, valine, selenocysteine and pyrrolysine, as well as any dipeptides, tripeptides or polypeptides formed by any combinations of these amino acids.

"Metal" means any metal known to be required as an essential element for the nutrition of humans, animals, or plant, including copper (Cu), zinc (Zn), iron (Fe), chromium (Cr), cobalt (Co), magnesium (Mg), manganese (Mn), selenium (Se), boron (Bo), and molybdenum (Mb) among others. As referred to herein, the "metal" can be in the form of a hydroxide or oxide.

"High solubility" means that the pure amino acid chelates of the present invention are very soluble in water and furthermore, are soluble in a broad pH range as exemplified by the range of 2-11 without the requirement for the addition of supplementary solubilizing agents.

"High stability" means that the pure amino acid chelates of the present invention are stable for extended periods of time when solubilized in: (a) a solvent having a pH from the range of 2-11, and/or (b) a phosphoric acid or citric acid solution or in a solution containing therein phosphoric acid and/or citric acid, and/or (c) beverages such as fruit drinks, and/or milk, without the need for the addition of supplementary stabilizing agents.

"Taste-free" means that the pure amino acid chelates of the present invention are tasteless or alternatively, do not have an unpleasant taste in comparison with pure water.

The methods of the present invention for preparing pure amino acid chelates, comprise two stages. The first stage generally comprises a one-step process for preparing a metal hydroxyl L-amino acetate. The second stage generally comprises three steps for preparing pure amino acid chelates wherein: (a) the molar ratio of metal to ligand is 1:4, and (b) the number of bonds between metal and amino acid ligands are equal to the coordination number of the central metal ion. It is to be noted that the methods of the present invention can be satisfactorily performed at ambient temperatures as exemplified by those selected from the range of 10° C. to 35° C. However, the reaction time period for the completing the two-stage methods of the present invention can be reduced, if so desired, by controllably heating the reaction vessels, for example, to temperatures selected from the range of 35° C. to 80° C.

The reactions used to prepare amino acid chelates without any interfering ions are shown in formulas 1 to 4.

Stage 1: production of a metal hydroxyl α-amino acetate.

$$Me(OH)_2 + HA^1 \rightarrow A^1MeOH \quad (1)$$

wherein $HA^1$ can be any L-amino acid, or a dipeptide, or a tripeptide or a polypeptide.

Stage 2: conversion of the metal hydroxyl α-amino acetate into an amino acid chelate.

$$A^1MeOH + HA^2 \rightarrow MeA^1A^2 \quad (2)$$

wherein $HA^2$ can be any L-amino acid, or a dipeptide, or a tripeptide or a polypeptide.

$$HA^3 + MeA^1A^2 \rightarrow MeA^1A^2A^3 \quad (3)$$

wherein $HA^3$ can be any L-amino acid, or a dipeptide, or a tripeptide or a polypeptide.

$$HA^4 + MeA^1A^2A^3 \rightarrow MeA^1A^2A^3A^4 \quad (4)$$

wherein $HA^4$ can be any L-amino acid, or a dipeptide, or a tripeptide or a polypeptide.

Those skilled in these arts will understand that the pH of the amino acid chelate product produced by reaction (4) according to the methods of the present invention, can be affected by the amino acids that have been selected for the preceding stage 1 and stage 2 reactions and for reaction (4).

Reaction (4) produces a transparent solution containing therein an amino acid chelate of the present invention. The transparent solution is preferably filtered, and then the reaction product i.e., the amino acid chelate, is dried to solids. Those skilled in these arts will understand that a variety of drying equipment as exemplified by spray driers, drum dryers, fluidized bed driers, flash driers, rotary evaporators, conveyer tray driers, vacuum driers and the like, can be employed for this purpose in one-step or multi-step processes thereby producing a dried amino acid chelate.

For each of the methods of the present invention, it is preferred that at least one of $HA^1$, $HA^2$, $HA^3$ and $HA^4$ comprises aspartic acid or glutamic acid. $HA^1$, $HA^2$, $HA^3$ and $HA^4$ may optionally comprise at least two different amino acids. Those skilled in these arts will understand that the aspartic and glutamic acid ligands in the amino acid chelates of the present invention can function as pH adjustors and/or stabilizers, and furthermore, may enhance the solubility of the amino acid chelates in certain solvents.

The pure amino acid chelates of the present invention produced by the methods of the present invention as described above, have generally possess the following physico-chemical attributes:

First; the pH of the final amino acid chelate product can be precisely controlled to a target specification by selecting and varying the combinations of different amino acids for reacting with the selected metal ion, thereby enabling the production of amino acid chelates that do not require the supplemental addition of pH adjustors or pH buffering systems for optimal absorption of minerals and amino acids in the intestines of humans and animals.

Second; the amino acid chelates of the present invention are very soluble in water, and may even be used to prepare highly concentrated syrups.

Third, the amino acid chelates of the present invention are very stable for extended time periods in solutions having very low pHs e.g., pH 2, and in solutions having very high pHs e.g., pH 11. Furthermore, the amino acid chelates of the present invention are stable in acidic beverages, fruit juices and milk. The solubility and stability attributes of the amino acid chelates of the present invention are particularly suited to a wide range of applications for incorporation into pharmaceutical and food compositions.

Fourth; since the amino acid chelates of the present invention are produced with methods that do not incorporate sulphate or chloride ion-containing substrates, they are free of such extraneous anions. Consequently, the amino acid chelates of the present invention are essentially taste-free. We surprisingly found that a cobalt amino acid produced with a method of the present invention had a sweet taste.

Those skilled in these arts will understand that chelation characteristics of the products produced by the methods of the present invention can be analyzed by infrared spectra (IR) and nuclear magnetic resonance (NMR), and that the molecular size of amino acid chelates can be determined by LC/MS.

Those skilled in these arts will understand that the concentrations of metal ions reported for prior art amino acid chelates are based on calculation of the molar ratio of metal/ligand, and that other anions such as sulphate or chloride ions may form bonds with the metal, particularly when pH adjusting, solubilising, or stabilising chemicals are added to the amino acid chelates. It should be noted that the methods of the present invention for producing amino acid chelates of the present invention react only metal oxides or metal hydroxides with amino acid ligands and therefore, the number bonds formed between the metal and the ligands will be equal to the coordination number of the central metal ion. Consequently, the metal contents of the amino acid chelates of the present invention are not based on molar ratio calculations of the metal/ligand, but rather, are based on the actual numbers of ligands bonding to the central metal ion and therefore, the values will be significantly lower than reported for the prior art amino acid chelates.

The essentially pure amino acid chelates of the present invention produced as described herein are particularly suited for incorporation into compositions suitable for nutrition of humans, animals and avian species. Exemplary embodiments of such compositions include beverages, foodstuffs, nutritional supplements, nutriceutical powders, tablets, capsules and liquids, and pharmaceutical adjuvants.

EXAMPLES

The following examples exemplify the methods, the amino acid chelates, and the compositions of the present invention. These examples are intended to illustrate how the methods of our invention can be employed and should not be considered to limit the scope of our invention.

Example 1

3.7923 g of aspartic acid were dissolved in 200 mL of distilled water after which, 2.1100 g of calcium hydroxide were added to the solution and stirred for 20 minutes, after which time, the pH was determined to be 10.30. Then, 4.3433 g of glycine were added into the reaction solution and stirred for 30 minutes, after which time, the pH was measured again and determined to be 8.75. Finally, 3.9098 g of aspartic acid were added to the reaction mixture and stirred for 40 minutes, thereby producing a clear reaction solution with a pH of 6.83 and containing therein the final reaction product. The chelate-containing solution was evaporated in a rotary evaporator (Tokyo Rikakikai Co., Ltd. Eyela Digital Water Bath SB-1000) and the chelate was finally dried to solids under vacuum supplied by a vacuum pump (Gardner Denver Welch Vacuum Technology, Inc., Skokie, Ill., USA. Welch 1400). This method produced a pure amino acid chelate with a ratio of calcium to amino acid of about 1:4 (Ca:2Asp:2Gly). FT-IR, two-dimensional NMR and LC/MS analyses of the Ca:2Asp:2Gly amino acid chelate product showed that there were no unbound free amino acid residues remaining in the product and four amino acid ligands were bound to the metal ion.

Example 2

Aspartic acid (3.7912 g) was dissolved in 200 mL of water and calcium hydroxide (2.1094 g) was added to react for 20 minutes. At this time the pH of solution was 10.30 and relatively stable. Next, 5.9866 g of serine was added and stirred until pH of solution dropped to 8.52 and stable (approximately 30 minutes). Finally, 3.7862 g of the aspartic acid was added to allow reacting for 105 minutes. The final solution was clear with pH 6.89. Water was evaporated in the rotary evaporator and the chelate was dried to solids under vacuum. This method produced a pure amino acid chelate with a ratio of calcium to amino acid of about 1:4 (Ca:2Asp:2Ser).

Example 3

A reaction solution comprised of 3.7985 g of aspartic acid, 2.1135 g of calcium hydroxide and 200 mL of water was prepared and allowed to react for 20 minutes while kept stirring. When the pH of the reaction solution reached and stabilized at 10.30, 6.7999 g of threonine were added and stirred for about 30 minutes until pH dropped to and stabilized at 8.50. Then, 3.8012 g of the aspartic acid were added and stirred for 120 minutes. The final solution produced at the end of the 120-min time period was clear with a pH of 6.90. The final solution was evaporated in a rotary evaporator (Tokyo Rikakikai Co., Ltd. Eyela Digital Water Bath SB-1000), and then further dried to solids under vacuum (Gardner Denver Welch Vacuum Technology, Inc., Skokie, Ill., USA. Welch 1400). The final product was a white powder comprising pure calcium amino acid chelate with a metal to amino acid ratio of about 1:4 (Ca:2Asp:2Thr).

Example 4

3.8101 g of aspartic acid were dissolved in 200 mL of water after which, 2.1199 g of calcium hydroxide were added to the reaction solution which was then stirred for about 20 minutes until the pH of solution stabilized at 10.40. 8.3634 g of lysine were then added to solution and stirred for another 30 min until the pH of solution dropped to 9.91. Finally, 3.8091 g of the aspartic acid were added and allowed to react in the solution for 70 minutes. The final solution produced was clear with a pH of 9.09. Water was evaporated from the solution in a rotary evaporator and the amino acid chelate product was further dried under vacuum. The final product was a white powder comprising pure calcium amino acid chelate with a metal to amino acid ratio of about 1:4 (Ca:2Asp:2Lys).

Example 5

A reaction solution was prepared by adding 3.6938 g of aspartic acid and 2.0707 g of calcium hydroxide in 200 mL of water, and then stirring the solution for about 48 minutes after which the pH of solution was determined to be 10.80. 2.0978 g of glycine were then added and the solution was further stirred until pH dropped to and stabilized at 9.60. Next, 4.1663 g of methionine were added to the reaction solution and then stirred for approximately 35 minutes after which the pH of solution was determined to be 9.12. Finally 3.7495 g of the aspartic acid were added to the solution which was stirred further for about 130 minutes after which its pH was determined to be 6.71. The final amino acid chelate containing solution was evaporated in the rotary evaporator to remove the water and then the chelate product was dried under vacuum. The final product was a pure calcium amino acid chelate powder with ratio of metal to amino acid 1:4 (Ca:2Asp:Gly:Met).

FT-IR, two-dimensional NMR and LC/MS analyses of the Ca:2Asp:Gly:Met amino acid chelate product showed there were no unbound free amino acid residues remaining in the product and the four amino acid ligands were bound to the metal ion.

Example 6

4.2482 g of glutamine acid were dissolved in 200 mL of water by stirring after which, 2.1407 g of calcium hydroxide were added and the solution further stirred for about 20 minutes until the pH of reaction solution was about 10.44. 3.4476 g of threonine were then added and the reaction solution stirred for another 30 minutes during which time the solution pH of solution dropped to and stabilized at 9.08. Next, 3.0383 g of serine were added and the reaction solution stirred for 20 minutes after which time it was determined that the pH of the reaction solution dropped to 8.72. Finally, 3.4630 g of aspartic acid were added to the reaction solution which was then stirred for a further 190 minutes. The pH of the final clear reaction solution was pH 7.00. The final reaction solution was filtered, then evaporated in the rotary evaporator after which, the amino acid chelate product was dried to solids under vacuum as previously described. This method produced a pure amino acid chelate with a metal to amino acid ratio of about 1:4 (Ca:Glu:Thr:Ser:Asp).

Example 7

3.7117 g of aspartic acid were dissolved in 200 mL of water after which 1.7043 g of magnesium hydroxide were added to aspartic acid solution, which was the further stirred for about 30 minutes after which the pH of the solution was determined to be 9.26 and stable. 3.3213 g of threonine were then added and the reaction solution mixed for about 100 minutes during which time its pH dropped to 8.79. Next, 2.9309 g of serine were added to the reaction solution which was then stirred for a further 35 minutes during which time the pH of solution dropped to 8.54. Finally, 4.0622 g of glutamic acid were added to the reaction solution which was then stirred further for about 190 minutes. The pH of the final clear reaction solution was determined to be pH 6.80. The final reaction was solution was filtered after which the water was removed by evaporation in a rotary evaporator and then the amino acid chelate product was dried under vacuum. The final product was a pure magnesium amino acid chelate having a metal to amino acid ratio of 1:4 (Mg:Asp:Thr:Ser:Glu).

Example 8

3.7086 g of aspartic acid was dissolved in 200 mL of water after which 2.5539 g of cobalt hydroxide were added and stirred further for about 45 minutes until the pH of solution reached 5.99. 4.8528 g of arginine were then added to the reaction solution which was then stirred for about 120 minutes during which the pH of the solution increased to 8.45. Next, 2.0093 g of glycine were added to the reaction mixture which was then stirred for about 150 minutes during which time the pH of the solution dropped to 7.86. Finally, 4.0973 g of glutamic acid were added and the reaction solution stirred for about 12 hours. The pH of the final reaction solution was 5.99. The final reaction solution was filtered after which the water removed by evaporation in a rotary evaporator. The amino acid chelate left behind was dried under vacuum. The final product was a pure cobalt amino acid chelate having a metal to amino acid ratio of about 1:4 (Co:Asp:Arg:Gly:Glu).

Example 9

3.7539 g of aspartic acid was dissolved in 200 mL of water after which, 2.6258 g of cobalt hydroxide were added to the reaction solution and stirred for another 45 minutes during after which the pH of the reaction solution was determined to be about 6.27. 3.3595 g of threonine were then added reaction solution for 60 minutes. The pH of the reaction solution was dropped to 5.86 and relatively stable. Next, 4.9131 g of arginine were added to the reaction solution which was stirred further for about for 50 minutes during which time the solution pH increased to 7.66. Finally, 2.1154 g of glycine were added to the reaction solution which was stirred for another 240 minutes during which time the solution pH stabilized at 7.56. The final clear reaction solution was evaporated in a rotary evaporator and the amino acid chelate product was dried to solids under vacuum. This method produced a pure cobalt amino acid chelate product with a metal to amino acid ratio of 1:4 (Co:Asp:Thr:Arg:Gly).

Example 10

3.8163 g of aspartic acid were dissolved in 200 mL of water after which, 2.3252 g of zinc oxide were added. The reaction solution was then stirred for about 2.5 hours after which time the pH was determined to be 6.73. 9.9882 g of arginine were then added to the reaction solution which was then stirred for about 1 hour during which time the reaction solution pH increased to 9.51. Finally, 3.8150 g of aspartic acid were added to the reaction solution which was then stirred for another 4 hours after which time, its pH was determined to be 7.40. The final reaction solution was filtered after which the water was evaporated, and the reaction product dried under vacuum. The final product was a pure zinc amino acid chelate with a metal to amino acid ratio 1:4 (Zn:2Asp:2Arg).

Example 11

3.7482 g of aspartic acid were dissolved in 200 mL of water to which, 2.2833 g of zinc oxide were added and the reaction solution then stirred for about 2 hours after which its pH was determined to be 6.66. Next, 8.2299 g of lysine were added to the reaction solution which was then stirred into the solution for 60 minutes during which time the solution pH increased to 9.35. Finally, 3.7490 g of aspartic acid were added to the reaction solution which was then stirred for about 12 hours. The pH of the final reaction solution was 7.64. The final reaction solution was filtered, then evaporated and the resulting solids were then dried under vacuum. This method produced a pure zinc amino acid chelate with a metal to amino acid ratio of about 1:4 (Zn:2Asp:2Lys).

Example 12

3.7036 g of aspartic acid were dissolved in 200 mL of water. 2.7186 g of cupric hydroxide were then added to the reaction solution which was stirred further for 30 minutes after which its pH was determined to be 4.11. Next, 8.154 g of lysine were added into the reaction solution which was then stirred for another 60 minutes during which time the pH increased to 9.74. Finally, 3.7041 g of aspartic acid were added into the reaction solution which was stirred for a further 90 minutes during which time the reaction solution dropped to and stabilized at 5.81. The final clear reaction solution was filtered, evaporated, and then dried to solids under vacuum. The final product was a pure copper chelate with a metal to amino acid ligand ratio 1:4 (Cu:2Asp:2Lys).

Example 13

1.0081 g of cupric hydroxide (1.0081 g) and 3.2103 g of histidine were mixed with 200 mL of water and stirred for 3 hours after which the pH of the reaction solution was determined to be 9.31. 1.3802 g of aspartic acid were then added to the reaction solution and stirred for 45 minutes after which the pH of reaction solution was determined to be 6.49. Finally, 0.7817 g of glycine were added into reaction solution which was then stirred for 30 minutes more during which time the pH stabilised at 6.52. The final clear reaction solution was filtered, then evaporated after which the reaction product was dried to solids under vacuum as previously described. This method produced a pure copper amino acid chelate with a metal to amino acid ligand ratio 1:4 (Cu:Asp:2His:1Gly).

Example 14

Table 1 lists eleven different metal amino acid chelates of the present invention prepared using the methods of the present invention as generally described above. Each of the metal amino acids was tested for solubility and stability in four types of acidic solutions i.e., (1) hydrochloric acid diluted with distilled water to a pH of 3.5, (2) hydrochloric acid diluted with distilled water to a pH of 2, (3) phosphoric acid diluted with distilled water to a pH of 3.5, (4) phosphoric acid diluted to a pH of 2; two basic solutions i.e., (1) sodium hydroxide diluted with distilled water to a pH of 11, (2) sodium hydroxide diluted with distilled water to a pH of 9); in orange juice (pH 3.76); and in milk (pH 6.66). A 0.2 g sample of each amino acid chelate was dissolved in a 5-mL volume of the test solution, and then stored at 22° C. (for acidic solutions and basic solutions) or at 4° C. (for orange juice and milk) for four weeks after which, the solutions were examined for the presence of precipitates. Table 1 shows that none of the samples tested showed evidence of precipitation after 4 weeks.

TABLE 1

Stability of the Amino Acid Chelates of the present invention in acidic and basic solutions, in orange juice and in milk, after a four-week storage period.

| Amino acid chelate composition | Hydrochloric acid | | Phosphoric acid | | Sodium hydroxide | | Milk (2% fat) | Orange juice |
| --- | --- | --- | --- | --- | --- | --- | --- | --- |
| | pH 3.5 | pH 2 | pH 3.5 | pH 2 | pH 11 | pH 9 | | |
| Ca:2Gly:2Asp | C* | C | C | C | C | C | C | C |
| Ca:Glu:Thr:Ser:Asp | C | C | C | C | C | C | C | C |
| Ca:2Asp:Gly:Met | C | C | C | C | C | C | C | C |
| Ca:2Asp:Gly:Met | C | C | C | C | C | C | C | C |
| Ca:2Asp:2Met | C | C | C | C | C | C | C | C |

TABLE 1-continued

Stability of the Amino Acid Chelates of the present invention in acidic and basic solutions, in orange juice and in milk, after a four-week storage period.

| Amino acid chelate composition | Hydrochloric acid | | Phosphoric acid | | Sodium hydroxide | | Milk (2% fat) | Orange juice |
|---|---|---|---|---|---|---|---|---|
| | pH 3.5 | pH 2 | pH 3.5 | pH 2 | pH 11 | pH 9 | | |
| Ca:2Asp:2Ser | C | C | C | C | C | C | C | C |
| Zn:2Asp:Arg | C | C | C | C | C | C | C | C |
| Zn:2Asp:2Lys | C | C | C | C | C | C | C | C |
| Co:Asp:Thr:Arg:Gly | C | C | C | C | C | C | C | C |
| Co:Asp:Arg:Gly:Clu | C | C | C | C | C | C | C | C |
| Cu:2His:Asp:Gly | C | C | C | C | C | C | C | C |

*Clear

While this invention has been described with respect to the preferred embodiments, it is to be understood that the various alterations and modifications can be made to the methods for producing amino acid chelates and the amino acid chelates so produced within the scope of this invention, which are limited only by the scope of the appended claims.

We claim:

1. A method of preparing pure amino acid chelates, said method consisting of:
   a first stage wherein a metal ion selected from the group comprising metal oxides and metal hydroxides, is contacted with an amino acid in a solvent thereby producing a solution comprising a metal hydroxyl amino acetate product;
   a second stage wherein said solution comprising said metal hydroxyl amino acetate product is contacted with at least one amino-containing compound selected from the group consisting of amino acids, dipeptides, tripeptides and polypeptides, said amino acids selected from the group consisting of alanine, arginine, asparagine, aspartic acid, creatine, cysteine, cystine, glutamic acid, glutamine, glycine, histidine, isoleucine, leucine, lysine, methionine, omithine, phenylalanine, proline, serine, threonine, tryptophane, tyrosine, valine, selenocysteine and pyrrolysine, said amino-containing compound provided in excess thereby producing a reaction solution containing therein a reaction product comprising a metal ion bound to a plurality of amino acid ligands, said plurality of amino acid ligands equal to the coordination number of the metal ion; and
   separating said reaction product from said reaction solution and drying said separated reaction product.

2. A method according to claim 1, wherein said metal ion is selected from the group consisting of boron, calcium, chromium, cobalt, copper, iron, magnesium, manganese, molybdenum, selenium and zinc.

* * * * *